(12) United States Patent
Trimper et al.

(10) Patent No.: US 8,612,353 B2
(45) Date of Patent: Dec. 17, 2013

(54) PUBLISHING INGESTED VIDEO CONTENT TO A VIDEO PROVISIONING SYSTEM

(75) Inventors: John K. Trimper, Groton, MA (US); Arthur C. Claxton, Vienna, VA (US)

(73) Assignees: Verizon Patent and Licensing Inc., Basking Ridge, NJ (US); Verizon Virginia LLC, Ashburn, VA (US)

( * ) Notice: Subject to any disclaimer, the term of this patent is extended or adjusted under 35 U.S.C. 154(b) by 163 days.

(21) Appl. No.: 13/196,776

(22) Filed: Aug. 2, 2011

(65) Prior Publication Data

US 2012/0079528 A1 Mar. 29, 2012

Related U.S. Application Data

(60) Provisional application No. 61/387,939, filed on Sep. 29, 2010.

(51) Int. Cl.
*G06Q 99/00* (2006.01)

(52) U.S. Cl.
USPC .............................................. 705/51; 725/39

(58) Field of Classification Search
USPC .............................................. 705/51; 725/39
See application file for complete search history.

(56) References Cited

U.S. PATENT DOCUMENTS

| | | | | |
|---|---|---|---|---|
| 5,664,109 A * | 9/1997 | Johnson et al. | ................... | 705/2 |
| 5,892,900 A * | 4/1999 | Ginter et al. | ................... | 726/26 |
| 6,031,927 A * | 2/2000 | Rao et al. | ...................... | 382/100 |
| 7,493,341 B2 * | 2/2009 | Israel et al. | ........................... | 1/1 |
| 7,818,444 B2 * | 10/2010 | Brueck et al. | ................. | 709/231 |
| 7,886,318 B2 * | 2/2011 | Wang et al. | ..................... | 725/25 |
| 8,161,082 B2 * | 4/2012 | Israel et al. | .................... | 707/803 |
| 8,244,639 B2 * | 8/2012 | Levy | ............... | 705/51 |
| 8,392,959 B2 * | 3/2013 | Cook | ........................... | 725/133 |
| 2006/0156388 A1 * | 7/2006 | Stirbu et al. | ........................ | 726/4 |
| 2007/0124781 A1 * | 5/2007 | Casey et al. | ....................... | 725/94 |
| 2007/0226365 A1 * | 9/2007 | Hildreth et al. | ............... | 709/231 |
| 2008/0195743 A1 * | 8/2008 | Brueck et al. | ................. | 709/231 |
| 2008/0320543 A1 * | 12/2008 | Wang et al. | .................... | 725/131 |
| 2009/0006211 A1 * | 1/2009 | Perry et al. | ....................... | 705/14 |
| 2009/0150735 A1 * | 6/2009 | Israel et al. | ................... | 714/746 |
| 2010/0100899 A1 * | 4/2010 | Bradbury et al. | ............... | 725/29 |
| 2010/0281508 A1 * | 11/2010 | Poder et al. | ..................... | 725/93 |
| 2010/0319017 A1 * | 12/2010 | Cook | ............................. | 725/31 |

(Continued)

OTHER PUBLICATIONS

Schneier, Applied Cryptography: Protocols, Algorithms, and Source Code in C, 1996, John Wiley and Sons, Inc., pp. 4 and 28.*

(Continued)

*Primary Examiner* — James D Nigh

(57) ABSTRACT

A system may receive an instruction to publish a video asset to a video provisioning system; retrieve profiles associated with the video asset, where a first profile may correspond to a set top box (STB) and a second profile may correspond to another device of a different type than the STB; process the video asset to create a first asset that can be published to a first device, associated with the system, based on the first profile; and process the video asset to create a second asset can be published to a second device, associated with the system, based on the second profile. The system may also publish the first asset to the first device that enables the STB to obtain the first asset from the first device; and publish the second asset to the second device that enables the other device to obtain the second asset from the second device.

22 Claims, 9 Drawing Sheets

600 ⟶

| PACKAGE ID 605 | |
|---|---|
| ASSET INFO 610 | ENCRYPTION 615 |
| USER DEVICE INFO 620 | AVAILABILITY 625 |

(56) References Cited

U.S. PATENT DOCUMENTS

2011/0235991 A1* 9/2011 Luthra et al. .................. 386/232
2011/0273618 A1* 11/2011 Takahashi et al. ............ 348/575
2012/0079054 A1* 3/2012 Moroney et al. .............. 709/213

OTHER PUBLICATIONS

C++ Plus Data Structures, Dale, Nell B., Boston, MA Jones & Bartlett Publishers, Inc., 2003., ISBN No. 9780763704810.*

"structured data Definition from PC Magazine Encyclopedia", http://www.pcmag.com/encyclopedia/term/52162/structured-data, retreived Jul. 9, 2013, 2 pages.*

"What is data structure?—A Word Definition from the Webopedia Computer Dictionary", retrieved from http://www.webopedia.com/TERM/D/data_structure.html, Jul. 9, 2013, 2 pages.*

"Teach-ICT A Level Computing OCR exam board—Define data structures", http://www.teach-ict.com/as_as_computing/ocr/H447/F453/3_3_5/data_structures/miniweb/pg2.htm, retreived Jul. 9, 2013, 1 page.*

"What is a computer network address?", http://compnetworking.about.com/od/basicnetworkingconcepts/g/bldef_address.htm, retrieved Jul. 9, 2013, 2 pages.*

* cited by examiner

PUBLISHING INGESTED VIDEO CONTENT TO A VIDEO PROVISIONING SYSTEM

REFERENCE TO RELATED APPLICATION

This application claims priority to U.S. Provisional Patent Application No. 61/387,939, filed Sep. 29, 2010, the entire contents of the provisional application being incorporated herein by reference.

BACKGROUND

Users, of user devices, have a growing array of sources, networks, and/or content providers from which to obtain video content and/or services. The users may use video client devices (e.g., a set top box, etc.) to obtain free broadcast television video content (e.g., from Fox, ABC, CBS, etc.), on-demand video content (e.g., Video On-Demand (VOD), pay-per-view (PPV), etc.), and/or pay television video content (e.g., from HBO, Cinemax, etc.) from cable television operators (e.g., Comcast, Time Warner, etc.) and/or satellite television operators (e.g., DirectTV, Dish Network, etc.). The users may use computer devices, wireless mobile handset devices, etc. to obtain other video content from on-line content providers, such as television operators (e.g., ABC, Fox, CBS, etc.), over-the-top (OTT) content providers (e.g., Hulu, Veoh, Jaman, YouTube, etc.), and/or other commercial content providers (e.g., Apple Computer's iTunes, Netflix, Blockbuster, etc.).

Unfortunately, the video content is not always received from content providers in a format and/or protocol that can be played by the different types of user devices. Additionally, it is sometimes difficult to offer and/or distribute the video content, to the different types of user devices and/or via different types of networks, to enable the different types of user devices to access, obtain, or play the video content.

DETAILED DESCRIPTION OF PREFERRED EMBODIMENTS

Figure 1:
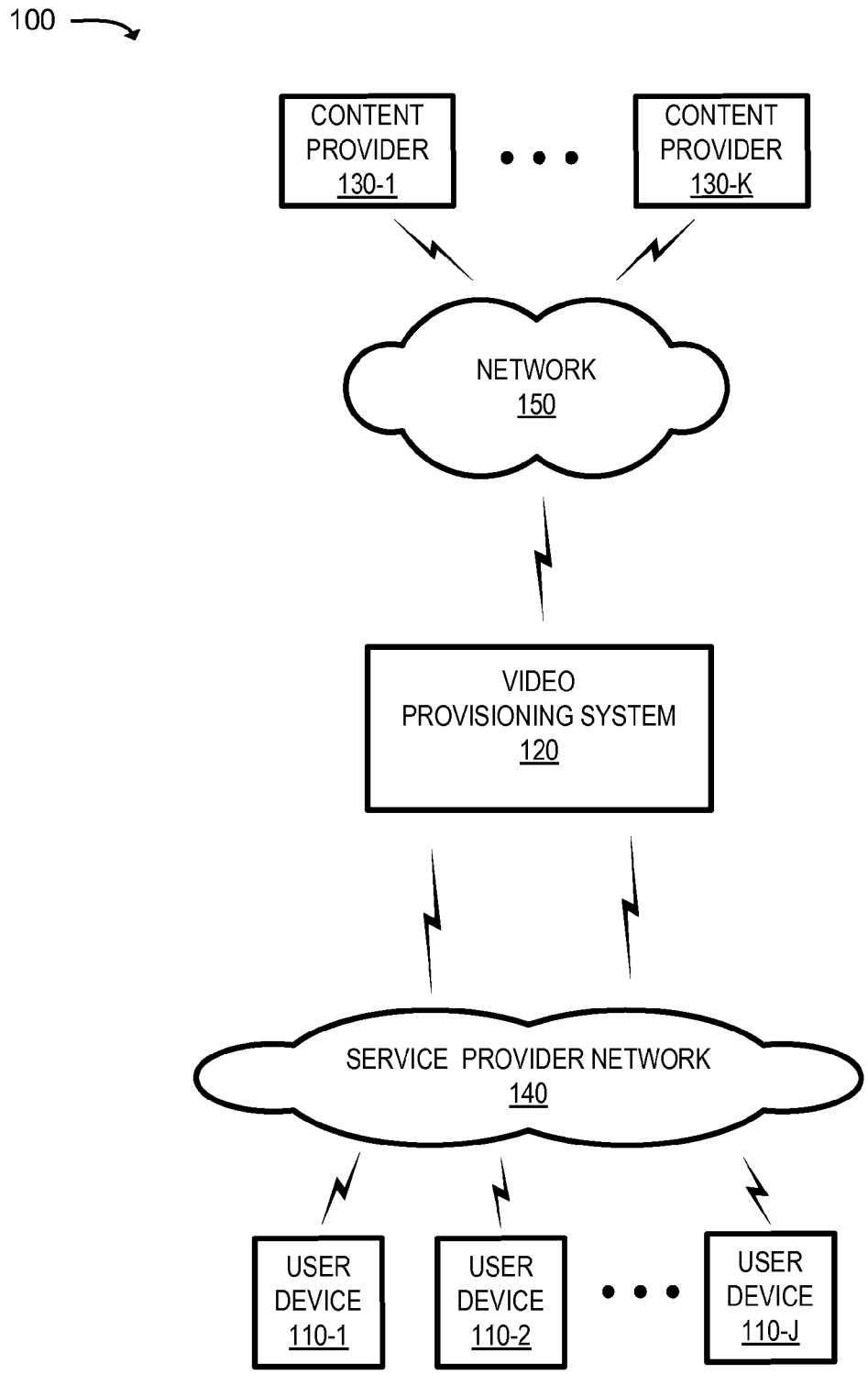
FIG. 1 is a diagram of an example environment in which the systems and/or methods, described herein, may be implemented.

The following detailed description refers to the accompanying drawings. The same reference numbers in different drawings may identify the same or similar elements.

Systems and/or methods, described herein, may enable video content, of different formats, which have been ingested and/or processed by a video content management system (VCMS), to be published to a video provisioning system. Publishing the video content to the video provisioning system may allow different types of user devices to access, obtain, and/or play the video content. The systems and/or methods may enable the VCMS to perform the publication operation by encrypting the video content video to create packaged video content. The packaged video content may include copies of the video content that are formatted to be played on the different types of user devices when the video content is available for release to the user devices. The systems and/or methods may enable the VCMS to publish the packaged video content to one or more destination devices, associated with the video provisioning system, from which the video asset can be obtained by the different types of user devices. The systems and/or methods may enable ingested metadata, associated with the packaged video content, to be published to a store front portal that allows the different types of user devices to access the metadata to download and/or play the video asset.

The different types of user devices may, for example, include computer devices (e.g., desktop computers, laptop computers, and tablet computers), wireless handset devices (e.g., mobile phones, smart phones, personal digital assistants (PDAs), and tablet computers), and/or set top boxes. Additionally, the video content may be provisioned to the various types of user devices via a number of different types of networks, such as, for example, a wired network, a wireless network, a broadband network, a cellular telephone network, a television network, etc., and/or some combination thereof.

The term video content, as used herein, may include one or more video assets, information associated with data rights management (DRM) (hereinafter referred to as "DRM information"), and/or metadata. The video assets may include Video On-Demand (VOD) video content, pay-per-view (PPV) video content, rented video content, free television content (e.g., from free television broadcasters, etc.), paid for television content (e.g., from pay television content providers), on-line video content (e.g., on-line television programs, movies, videos, etc.), advertising, games, music videos, promotional information (e.g., such as previews, trailers, etc.), etc. A video asset may be stored in one or more video files that contain video information that can be played on a user device.

The DRM information may include license information that identifies terms and/or conditions for handling, promoting, distributing, and/or using the video assets and/or enables video assets to be encrypted and/or decrypted (e.g., based on keys associated with the license information).

The metadata may enable the video assets to be identified, managed, offered, and/or distributed to a user device. The metadata may, for example, include an identifier associated with a video asset (e.g., a number, a name, a title, etc.); a genre of the video asset (e.g., horror, comedy, adult, etc.); a category of the video asset (e.g., VOD asset, a PPV asset, an on-line asset, etc.); a text description and/or summary of the video asset; an image (e.g., cover art) associated with the video asset, and/or information associated with artists associated with the video asset (e.g., names of actors, directors, producers, etc.). The metadata may also, or alternatively, include information associated with a type of video asset (e.g., a movie, music video, a game, etc.); a rating associated with the video asset (e.g., general audience (G), parental guidance (PG), PG-13, restricted (R), mature audience (MA), etc.); user reviews associated with the video asset; a price associated with the video asset (e.g., a sale price, a rental price per day, a pay-per-view price, etc.); and/or an availability period associated with the video asset (e.g., release dates, restriction periods, blackout periods, etc.). The metadata may also, or alternatively, include information associated with a storage location (e.g., a uniform resource locator (URL)) corresponding to the video asset; a format associated with the video asset (e.g., a resolution level, compression/decompression (CODEC) information, a screen size, a frame size, a frame refresh rate, a bit rate, etc.); and/or types of user devices supported by each format, etc.

FIG. 1 is a diagram of an example environment in which the systems and/or methods, described herein, may be implemented. As shown in FIG. 1, environment 100 may include a group of user devices 110-1, ..., 110-J (where J≥1) (hereinafter referred to collectively as "user devices 110" and individually as "user device 110"), a video provisioning system (VPS) 120, a group of content providers 130-1, ..., 130-K (where K≥1) (hereinafter referred to collectively as "content providers 130" and individually as "content provider 130"), a service provider network 140, and a network 150. The number of devices, systems, and/or networks, illustrated in FIG. 1, is provided for explanatory purposes only. In practice, there may be additional devices, systems, and/or networks; fewer devices, systems, and/or networks; different devices, systems, and/or networks; or differently arranged devices, systems, and/or networks than illustrated in FIG. 1.

Also, in some implementations, one or more of the devices of environment 100 may perform one or more functions described as being performed by another one or more of the devices of environment 100. Devices, systems, and/or networks of environment 100 may interconnect via wired connections, wireless connections, or a combination of wired and wireless connections.

User device 110 may include a computation or communication device that is capable of communicating with service provider network 140. For example, user device 110 may include a radiotelephone, a personal communications system (PCS) terminal (e.g., that may combine a cellular radiotelephone with data processing and data communications capabilities), a personal digital assistant (PDA) (e.g., that can include a radiotelephone, a pager, Internet/intranet access, etc.), a laptop computer, a tablet computer, a set top box, a digital video recorder (DVR), a personal gaming system, a smart phone, or another type of computation or communication device.

User device 110 may communicate with VPS 120 and/or perform certain operations to obtain a video asset from VPS 120. For example, user device 110 may access a portal (e.g., a website, a user interface, an interactive program guide, an interactive media guide, etc.) associated with VPS 120, to browse, search, select, and/or obtain a video asset. User device 110 may obtain DRM information, with respect to the video asset, and may use license information, obtained from the DRM information, to decrypt the video asset for playing on user device 110.

VPS 120 may include one or more devices that gather, process, search, store, and/or provide information in a manner similar to that described herein. VPS 120 may be capable of communicating with content providers 130 via network 150 and/or user devices 110 via service provider network 140. VPS 120 may provide a video provisioning service to user devices 110.

VPS 120 may, for example, perform operations associated with video content ingestion, processing, and/or distribution for one or more types of user devices 110, associated with a user, within environment 100. VPS 120 may communicate with one or more content providers 130 to acquire video content. VPS 120 may connect to a collection of various types of user devices 110 associated with a user, such as, for example, a set top box, a computer device, a wireless handset device (e.g., a smart phone, a personal digital assistant (PDA), etc.), and/or other types of user devices 110. VPS 120 may connect to the set top box via a television service provider network 140 (e.g., a cable television network, a satellite television network, a fiber optic television network, or some combination thereof). VPS 120 may connect to the computer device via a broad band service provider network 140 (e.g., via the Internet). VPS 120 may connect to the wireless handset device via a wireless service provider network 140. VPS 120 may perform an ingestion operation on the acquired video content. VPS 120 may process and/or publish the ingested video content in a manner that allows the video content to be offered and/or distributed to the different types of user devices 110.

Content provider 130 may include any type or form of content provider. For example, content provider 130 may include free television broadcast providers (e.g., local broadcast providers, such as NBC, CBS, ABC, and/or Fox), for-pay television broadcast providers (e.g., TNT, ESPN, HBO, Cinemax, CNN, etc.), and/or Internet-based content providers (e.g., Youtube, Vimeo, Netflix, Hulu, Veoh, etc.) that stream content from web sites and/or permit content to be downloaded (e.g., via progressive download, etc.). Content provider 130 may include on-demand content providers (e.g., VOD, PPV, etc.). A media stream, as used herein, may refer to a stream of content that includes video content (e.g., a video stream), audio content (e.g., an audio stream), and/or textual content (e.g., a textual stream).

Service provider network 140 may include one or more wired and/or wireless networks via which user devices 110 communicate with and/or receive video content from VPS 120. For example, service provider network 140 may include a cellular network, the Public Land Mobile Network (PLMN), a second generation (2G) network, a third generation (3G) network, a fourth generation (4G) network (e.g., a long term evolution (LTE) network), a fifth generation (5G) network, and/or another network. Additionally, or alternatively, service provider network 140 may include a code division multiple access (CDMA) network, a global system for mobile communications (GSM) network, a general packet radio services (GPRS) network, or a combination of CDMA, GSM, and/or GPRS networks. Additionally, or alternatively, service provider network 140 may include a wide area network (WAN), a metropolitan area network (MAN), an ad hoc network, an intranet, a fiber optic-based network (e.g., a fiber optic service (FiOS) network), a television network, and/or a combination of these or other types of networks.

Network 150 may include one or more wired and/or wireless networks. For example, network 150 may include a cellular network, the PLMN, a 2G network, a 3G network, a 4G network (e.g., an LTE network), a 5G network, and/or another network. Additionally, or alternatively, network 150 may include a WAN, a MAN, a telephone network (e.g., the Public Switched Telephone Network (PSTN)), an ad hoc network, an intranet, the Internet, a fiber optic-based network, and/or a combination of these or other types of networks.

Figure 2:
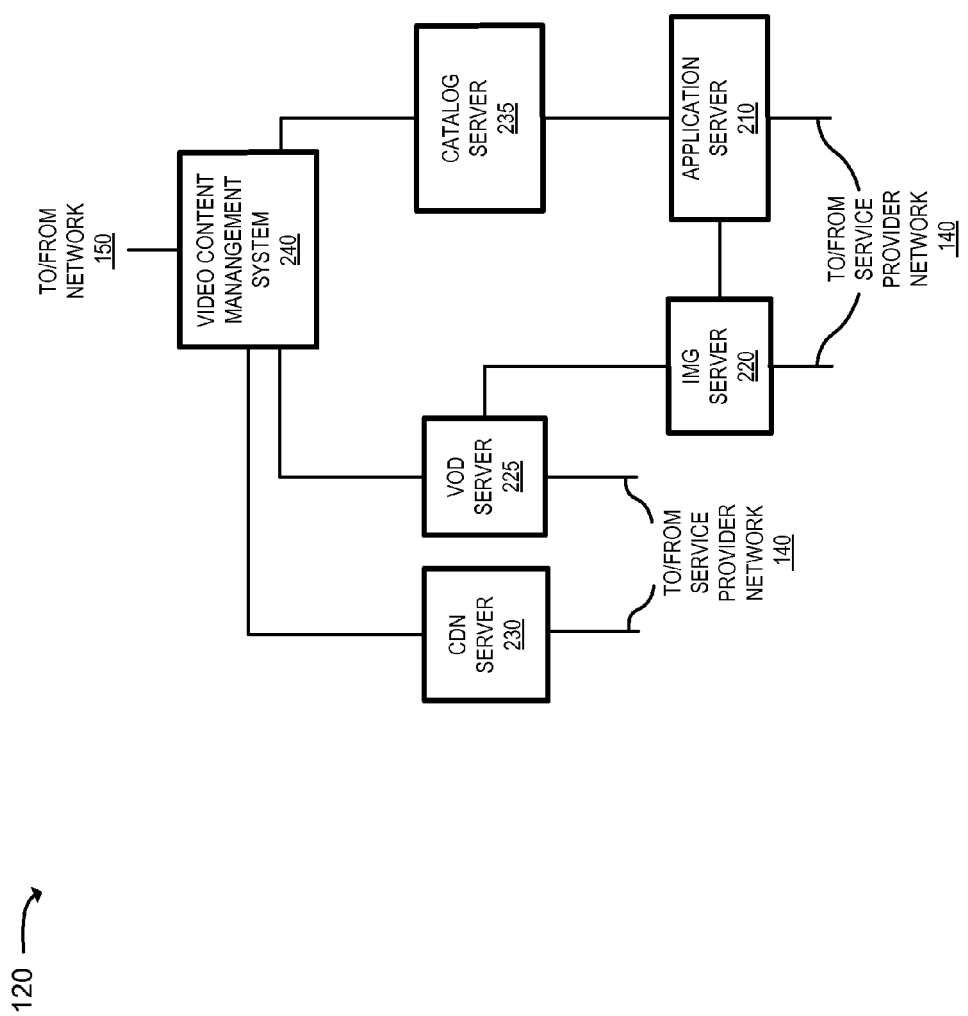
FIG. 2 is a diagram of example devices, associated with the video provisioning system, of FIG. 1.

FIG. 2 is a diagram of example devices associated with VPS 120. VPS 120 may include an application server 210, an interactive media guide (IMG) server 220, a video on-demand (VOD) server 225, a content delivery network (CDN) server 230, a catalog server 235, and a video content management (VCM) system 240. Although FIG. 2 shows example devices of VPS 120, in other implementations, VPS 120 may include fewer devices, additional devices, different devices, or differently arranged devices than depicted in FIG. 2. Additionally, or alternatively, one or more devices of VPS 120 may perform one or more tasks described as being performed by one or more other devices of VPS 120.

In the description below, VOD server 225 is described as provisioning video services for a type of user device 110 (i.e., a set top box) and CDN server 230 is described as provisioning video services for another type of user device 110 (i.e., a computer device, a wireless handset device, etc.) for explanatory purposes. In another implementation, the video services may be provisioned for the set top box and/or the other types of user devices 110 in a number of ways. For example, VOD server 225 and/or CDN server 230 may be combined into a single device that provisions the video services for each type of user device 110. In another example, the video services may be provisioned, for each type of user device 110, by another device and/or network instead of, or in combination with, VOD server 225 and/or CDN server 230. Additionally, IMG server 220 is described as providing a store front portal (i.e., via an IMG), that can be accessed by the set top box, and application server 210 is described as providing another store front portal (e.g., via a web page, a user interface, an interactive program guide, etc.), that can be accessed by the other types of user devices 110, for explanatory purposes. In another implementation, the store front portal may be provisioned for the set top box and/or the other types of user devices 110 in a number of ways. For example, IMG server 220 and/or application server 210 may be combined into a single device that provisions the store front portal for each type of user device 110. In another example, the store front portal may be provisioned, for each type of user device 110, by another device and/or network instead of, or in combination with, IMG server 220 and/or application server 210. Thus, the examples below are provided for explanatory purposes only.

Application server 210 may include one or more server devices, or other types of computation or communication devices, that gather, process, search, store, and/or provide information in a manner similar to that described herein. Application server 210 may receive metadata that has been published by catalog server 235. The metadata may be associated with video assets that are to be made available and/or offered (e.g., for sale, rent, subscription, etc.) to user devices 110. Application server 210 may host a portal (e.g., a VPS store front), such as a private website (e.g., for subscribing user devices 110), a public website (e.g., for non-subscribing user devices 110), a user interface (UI) (e.g., that is accessible by wireless handset user devices 110, etc.), an interactive program guide (e.g., an IMG for set top box-type user devices 110) and/or other types of user interfaces. The portal may enable single sign-on (SSO) portal access, to a user of one or more user devices 110, based on the same login credentials (e.g., username, password, personal identification number (PIN), etc.). Application server 210 may publish all or a portion of the metadata to the portal that permits any of user devices 110 to browse, perform searches, process payment, etc. for video assets based on the metadata that is published to the portal.

IMG server 220 may include one or more server devices, or other types of computation or communication devices, that gather, process, search, store, and/or provide information in a manner similar to that described herein. IMG server 220 may, for example, process metadata, that has been published by catalog server 235 and/or VOD server 225, in a manner similar to that described above (e.g., with respect to application server 210). The metadata may be associated with video content that may be obtained by a particular type of user device 110, such as a set top box user device 110.

IMG server 220 may publish all or a portion of the metadata to an IMG UI that the set top box user device 110, associated with the user, may render for display on a video display device. IMG server 220 may permit the set top box user device 110 to access information associated with video assets, stored by VOD server 225, and access the actual video assets. IMG server 220 may, in another example implementation, communicate with application server 210, which may permit the set top box user device 110 to access the metadata associated video assets that are stored in CDN server 230.

VOD server 225 may include one or more server devices, or other types of computation or communication devices, that gather, process, search, store, and/or provide information in a manner similar to that described herein. VOD server 225 may, for example, perform operations to receive, store, process, and/or distribute video content in a format that is supported by set top box user devices 110.

VOD server 225 may receive published video assets and/or metadata from VCM system 240. VOD server 225 may store the published video assets in a memory associated with VOD server 225. VOD server 225 may publish a portion of the metadata, associated with video assets (e.g., that are available for release and/or not subject to a blackout, etc.), to IMG server 220. In another example implementation, VOD server 225 may communicate with content provider 130 to receive video content directly from content provider 130 (e.g., not via VCM system 240).

CDN server 230 may include one or more server devices, or other types of computation or communication devices, that gather, process, search, store, and/or provide information in a manner similar to that described herein. CDN server 230 may, for example, perform operations to receive, store, process, and/or distribute video content in a format that is supported by one or more types of user devices 110 (e.g., a computer device, a wireless mobile device, a gaming device, etc.) other than, or in addition to, a set top box user device 110. CDN server 230 may actually represent a content delivery network that includes multiple routing and/or storage devices.

CDN server 230 may receive published video assets in multiple video formats from VCM system 240. CDN server 230 may store the published video assets in a memory associated with CDN server 230. CDN server 230 may identify a respective storage location and/or URL for each format of each video asset that are stored within the memory and may send information associated with the storage locations and/or the URLs to catalog server 235. CDN server 230 may provide video assets to wireless handset user devices 110 via a wireless service provider network 140. CDN server 230 may provide the video assets to a computer user device 110 via a broadband service provider network 140 (e.g., the Internet). In another example implementation, CDN server 230 may provide the video assets to a set top box user device 110 via a television service provider network 140 and/or via VOD server 225.

Catalog server 235 may include one or more server devices, or other types of computation or communication devices, that gather, process, search, store, and/or provide information in a manner similar to that described herein. Catalog server 235 may, for example, receive, from VCM system 240, published metadata associated with video assets that have been published to VOD server 225 and/or CDN server 230. Catalog server 235 may identify, from the metadata, information associated with the availability of the video assets based on dates on which the video assets are released, blacked out, etc. Catalog server 235 may process and/or package the metadata in order to offer, to user devices 110, the video assets to which the metadata corresponds. The processed metadata, associated with the video assets, may include identifiers (e.g., video asset numbers, titles, etc.), prices (e.g., sale prices, rental prices, subscription prices, etc.), descriptions (e.g., a synopsis, a summary, etc. of the video assets), ratings, reviews, genres, casting information (e.g., actors, directors, producers, etc.), etc. Catalog server 235 may, for example, publish the metadata to the store front portal associated with VPS 120. Catalog server 235 may not publish metadata associated with video assets that are identified as not yet being available.

VCM system 240 may include one or more server devices, or other types of computation or communication devices, that gather, process, search, store, and/or provide information in a manner similar to that described herein. VCM system 240 may, for example, communicate with content providers 130 to acquire high quality video content (e.g., video content that includes video assets associated with the resolution level and/or bit rate that is greater than a threshold) from content providers 130. VCM system 240 may perform an operation, on the acquired video content, that allows the video content to be ingested by VCM system 240. VCM system 240 may process the ingested video content so that the ingested video content is supported by different types of user devices 110 (e.g., set top boxes, computer devices, handheld wireless devices, gaming devices, etc.). Additionally, VCM system 240 may package the video content to prepare the video assets to be offered to user devices 110. VCM system 240 may publish the video content to one or more devices, associated with VPS 120, that allows the video content to be offered and/or distributed to the different types of user devices 110, via different types of service provider network 140, by VPS 120.

Figure 3:
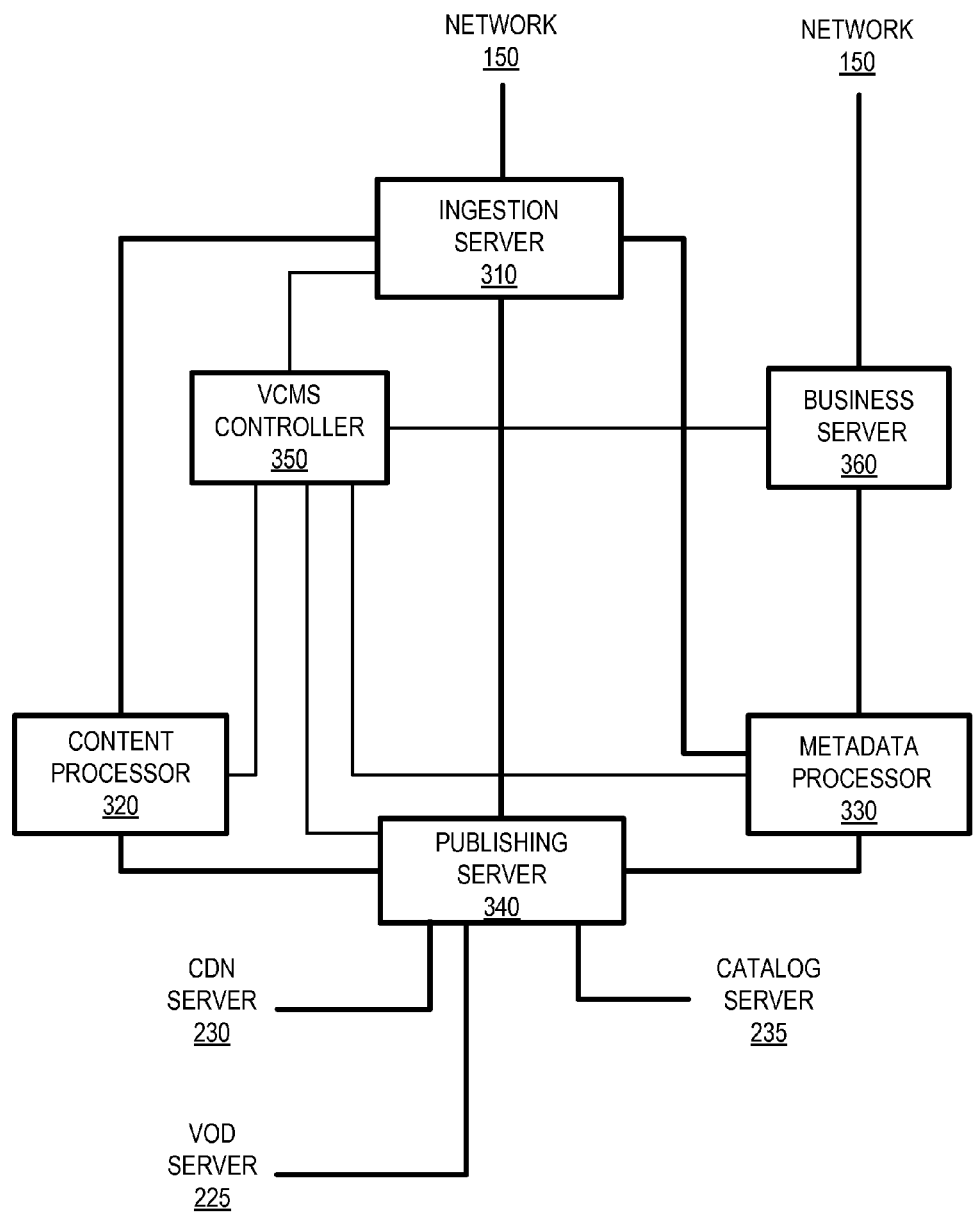
FIG. 3 is a diagram of example devices, associated with a video content management system, of FIG. 2.

FIG. 3 is a diagram of example devices associated with VCM system 240. VCM system 240 may include an ingestion server 310, a content processor 320, a metadata processor 330, a publishing server 340, a video content management system (VCMS) controller 350, and a business server 360. Although FIG. 3 shows example devices of VCM system 240, in other implementations, VCM system 240 may include fewer devices, additional devices, different devices, or differently arranged devices than depicted in FIG. 3. For example, some or all of the devices, associated with VCM system 240 could be combined into a single device. Additionally, or alternatively, one or more devices of VCM system 240 may perform one or more tasks described as being performed by one or more other devices of VCM system 240.

Ingestion server 310 may include one or more server devices, or other types of computation or communication devices, that gather, process, search, store, and/or provide information in a manner similar to that described herein. Ingestion server 310 may, for example, perform operations associated with acquiring and/or ingesting video content, for use by VPS 120, to provide a video provisioning service to the different types of user devices 110.

Ingestion server 310 may, for example, receive video content from communication server 130. Ingestion server 310 may temporarily store the acquired video content in a memory associated with VCM system 240 (e.g., sometimes referred to as an "ingest memory"). Ingestion server 310 may analyze the video content to verify that the video content is in a particular format, file type, etc., and/or is complete when acquired from content provider 130. Ingestion server 130 may decrypt video assets, metadata, etc., obtained from the video content, to allow further processing to be performed on the video assets, metadata, etc.

Content processor 320 may include one or more devices, or other types of computation or communication devices, that gather, process, search, store, and/or provide information in a manner similar to that described herein. Content processor 320 may process video assets received from ingestion server 310.

Content processor 320 may, for example, perform a quality operation on a video asset, received from ingest server 310 and/or retrieved from the ingest memory, to identify a condition (e.g., a gap within a video signal, a distorted video signal, etc.) associated with the video asset and/or to verify that the video asset conforms to a particular standard (e.g., video standard, an audio standard, etc.). Content processor 320 may repair the video asset to remedy the condition and/or to cause the video asset to comply with the particular standard. Content processor may obtain a copy of the video asset, from content provider 130, based on a determination that the video content cannot be repaired. Content processor may store the video asset, as a source video asset, in a memory associated with VCM system 240 (sometimes referred to as a "mezzanine memory").

Content processor 320 may use the source video asset to generate copies of the video asset. Content processor 320 may transcode each of the copies of the video asset to conform to respective formats that can be supported (e.g., received, processed, played, etc.) by different types of user devices 110 (e.g., set top boxes, computer devices, wireless mobile handsets, gaming devices, etc.). For example, each copy may correspond to respective different formats associated with unique bit rates, levels of resolution (e.g., standard definition, high definition, etc.), frame refresh rates, screen sizes (e.g., aspect ratios, dimensions, etc.), compression/decompression (CODEC) ratios, etc. that can be supported by wireless handset devices, computer devices, set top boxes, gaming devices, etc. In another example, content processor 320 may transcode other copies of the video asset to conform to other formats (e.g., high definition, standard definition, etc.). Content processor 320 may store the transcoded copies of the video assets in another memory associated with VCM system 240 (sometimes referred to as a "publish memory").

Content processor 320 may perform another quality operation on each copy of the video asset. The other quality operation may verify that the copy is not associated with a condition and/or can be played by a type of user device 110 for which the copy of the video asset was transcoded. If a condition is detected, content processor 320 may retranscode another copy of the video asset to ensure that the other copy of the video asset is not associated with a condition.

Metadata processor 330 may include one or more devices, or other types of computation or communication devices, that gather, process, search, store, and/or provide information in a manner similar to that described herein. Metadata processor 330 may process metadata received from ingestion server 310.

Metadata processor 330 may receive metadata from ingestion server 310 and/or may retrieve the metadata from the ingest memory and/or another memory (e.g., sometimes referred to as a "metadata repository"), associated with VCM system 240. Metadata server 330 may convert the metadata into a metadata format that conforms to a metadata standard (e.g., image standard, text standard, data standard, etc.) that is utilized by VPS 120 and/or specified by an operator associated with VPS 120.

Metadata processor 330 may generate copies of the metadata in different configurations or formats that can be supported by the different types of user devices 110. For example, metadata processor 330 may generate copies of images that conform to a screen size, an aspect ratio, a level of resolution etc., that is supported by the different types of user devices 110.

Metadata processor 330 may communicate with business server 360 to obtain other metadata associated with a video asset. The other metadata may identify a genre associated with the video asset (e.g., a drama, a western, a comedy, etc.), a price structure (e.g., a sale price, a rental price, a subscription price, etc.) associated with the video asset, information associated with a bundle (e.g., other video assets and/or services) with which the video asset is to be published, etc. Metadata processor 330 may combine the update metadata with the metadata.

Publishing server 340 may include one or more devices, or other types of computation or communication devices, that gather, process, search, store, and/or provide information in a manner similar to that described herein. Publishing server 340 may publish video assets that have been ingested and/or processed by VCM system 240. Publishing server 340 may publish the video assets to destination devices, such as VOD server 225 and/or CDN server 230, that enables different types of user devices 110 to access and/or obtain the video assets.

Publishing server 340 may publish video assets based on a video profile that identifies the manner in which the video assets are to be packaged for publishing. For example, the video profile may identify a package, associated with a video asset, based on a type of user device 110 on which the video asset is to be played. The video profile may identify a format of the video asset (e.g., screen size, aspect ratio, frame rate, bit rate, resolution level, CODEC, etc.) that can be supported by the type of user device 110, a type of encryption (e.g., based on DRM info, cable access system (CAS) encryption, etc.) to use to protect the video asset, when the video asset is available, etc. Publishing server 340 may retrieve, from the publish memory, one or more copies of the video asset (e.g., an image, video, a trailer, etc.), associated with a package, that correspond to the format of the video asset identified by the video profile. Publishing server 340 may retrieve information associated with the type of encryption (e.g., CAS information, DRM information) to be used to protect the package for publication.

Publishing server 340 may use publication information, retrieved from a memory associated with publishing server 340, to publish the package to a destination device associated with VPS 120. For example, the publication information may identify a network address (e.g., a URL, an IP address, etc.) associated with the destination device (e.g., VOD server 225) and/or information associated with an interface via which the package is to be published to the destination device. The publication information may also include access credentials (e.g., login credentials, such as username, password, etc.) associated with the destination device, information regarding a metadata format that is supported by the destination device, an indication whether metadata, associated with the package is to be published, etc.

Publishing server 340 may, for example, use the network address and/or access credentials to communicate with VOD server 225 to establish a connection via which the package, to be distributed to a set top box user device 110, may be transmitted for publication. Publishing server 340 may transmit the package to VOD server 225 via the interface identified in the publication information. In one example, publishing server 340 may transmit the package by streaming the package in a manner that encrypts the package (e.g., using the CAS information) as the package is being streamed to VOD server 225. VOD server 225 may receive the package and may store the package for distribution to a set top box.

Publishing server 340 may, in a manner similar to that described above, publish another package, associated with the video asset, to another destination device (e.g., CDN server 230). The other package may be associated with a different type of user device 110 (e.g., a computer device, a wireless handheld device, etc.). The other package may be published based on another video profile that is based on the different type of user device 110. Publishing server 340 may use other publication information, associated with CDN server 230, to publish the other package.

Publishing server 340 may, for example, use a network address and/or access credentials, obtained from the other publication information and/or the other video profile, respectively, to communicate with CDN server 230. Publishing server 340 may transmit the other package to CDN server 230 via another interface identified in the other publication information. Publishing server 340 may, in this example, encrypt the package using other encryption information (e.g., DRM information) identified in the other video profile. Publishing server 340 may transmit the encrypted package to CDN server 230 (e.g., using a progressive download protocol, adaptive bit-rate streaming, etc.). CDN server 230 may receive the other package and may store the other package for distribution to the different types of user devices 110.

Publishing server 340 may publish metadata, associated with the package based on a determination that the publication indicates that the metadata is to be published. Publishing server 340 may identify a format associated with the metadata based on the publication information and/or the video profile. The identified format may be supported by the type of user device 110 that accesses the metadata (e.g., via a store front portal) and/or may be specified by the destination device to which the metadata is to be published. Publishing server 340 may retrieve, from the publish memory and/or the metadata repository, a copy of metadata that conforms to the format. Publishing server 340 may publish the metadata by transmitting the metadata to the destination device. Publishing the metadata to a destination device, such as catalog server 235, may permit catalog server 235 to offer the video assets to the different types of user devices 110 via a store front portal (e.g., a web site, an interactive program guide, a user interface, etc.) that is hosted by application server 210. In another example, publishing server 340 may publish the metadata to another destination device, such as VOD server 225 and/or IMG server 220, which may permit the metadata to be accessible by set top box user devices 110 via another store front portal (e.g., an IMG) hosted by IMG server 220.

VCMS controller 350 may include one or more devices, or other types of computation or communication devices, that gather, process, search, store, and/or provide information in a manner similar to that described herein. VCMS controller 350 may be capable of communicating with ingestion server 310, content processor 320, metadata processor 330, publishing server 340, and/or business server 360. VCMS controller 350 may, for example, store logic that controls a workflow associated with ingesting, processing, and/or publishing video content to be used by VPS 120 to provide a video provisioning service to different types of user device 110. VCMS controller 350 may execute the workflow and send instructions to each device, associated with VCM system 240, while VCM system 240 is handling the video content.

VCMS controller 350 may, for example, send an instruction to ingestion server 310 that causes video content to be acquired from content provider 130. VCMS controller 350 may send instructions to content processor 320 and/or metadata processor 330 to ingest and/or process the acquired video content. VCMS controller 350 may send an instruction to business server 360 to provide information associated with a pricing structure for video assets that are to be published. VCMS controller 350 may send an instruction to publishing server 340 to publish the ingested and/or processed video content to one or more devices associated with VPS 120 for distribution to one or more types of user devices 110.

Business server 360 may include one or more devices, or other types of computation or communication devices, that gather, process, search, store, and/or provide information in a manner similar to that described herein. Business server 360 may perform business operations based on business rules that are programmed by an operator of business server 360 and/or incorporated into hardware associated with business server 360. Business server 360 may be capable of communicating with content provider 130, via network 150, to obtain contract information associated with video content to be ingested and/or published by VCM system 240. The contract information may include terms and/or conditions that define that manner and/or under what conditions video content may be provisioned to user device 110. The terms and/or conditions may specify a cost (e.g., to be paid to content provider 130) associated with the video content and/or a period of time during which the video content is available (e.g., a release date, a blackout period, etc.) to be distributed to user devices 110. In one example, the contract information may specify a minimum cost associated with each video asset rental, sale, subscription, etc. to be paid to a user of content provider 130. In another example, the cost may be specified as a percentage of a retail price (e.g., determined by VPS 120) for each video asset rental, sale, subscription price, etc. to be paid to the user of content provider 130.

Business server 360 may generate a price structure associated with the video content based on the contract information and the business rules associated with VPS 120. For example, business server 360 may generate a sale price that covers the cost identified in the contract information as well as other costs, such as operating costs associated with VPS 120, taxes, profit, etc. Business server 360 may, in a similar manner, generate a rental price, a subscription price, a price associated with the bundle of video assets, etc. Business server 360 may send the information associated with the price structure, availability, etc., to metadata processor 330, to be incorporated into metadata associated with the video asset.

Figure 4:
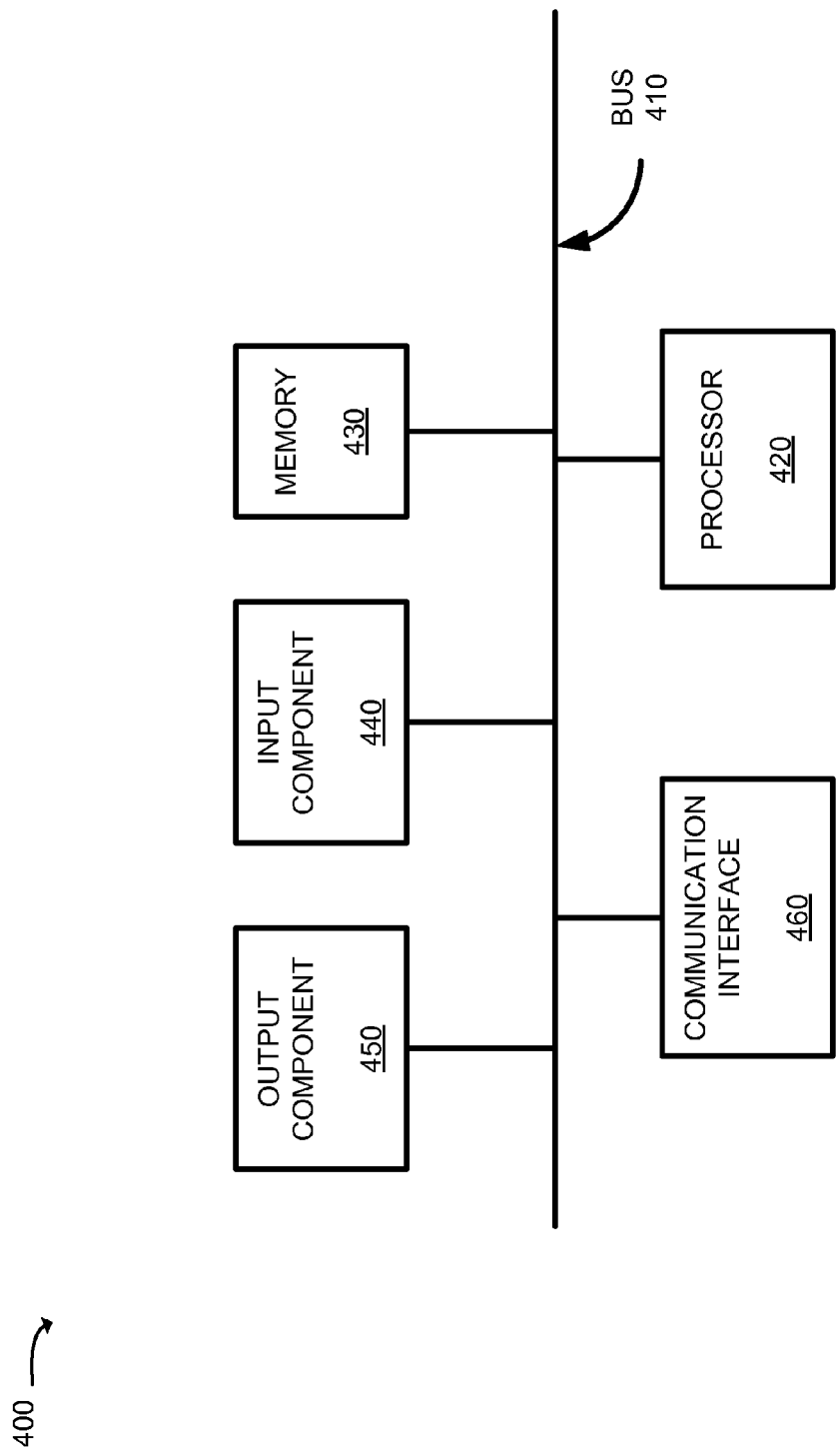
FIG. 4 is a diagram of example components that correspond to one or more of the devices of FIGS. 2 and/or 3.

FIG. 4 is a diagram of example components of a device 400 that may correspond to user device 110, content provider 130, application server 210, IMG server 220, VOD server 225, CDN server 230, catalog server 235, VCM system 240, ingestion server 310, content processor 320, metadata processor 330, publishing server 340, VCMS controller 350, and/or business server 360. Alternatively, each of user device 110, content provider 130, application server 210, IMG server 220, VOD server 225, CDN server 230, catalog server 235, VCM system 240, ingestion server 310, content processor 320, metadata processor 330, publishing server 340, VCMS controller 350, and/or business server 360 may include one or more devices 400. Device 400 may include a bus 410, a processor 420, a memory 430, an input component 440, an output component 450, and a communication interface 460. Although FIG. 4 shows example components of device 400, in other implementations, device 400 may contain fewer components, additional components, different components, or differently arranged components than depicted in FIG. 4. For example, device 400 may include one or more switch fabrics instead of, or in addition to, bus 410. Additionally, or alternatively, one or more components of device 400 may perform one or more tasks described as being performed by one or more other components of device 400.

Bus 410 may include a path that permits communication among the components of device 400. Processor 420 may include a processor, microprocessor, or processing logic that may interpret and execute instructions. Memory 430 may include any type of dynamic storage device that may store information and instructions, for execution by processor 420, and/or any type of non-volatile storage device that may store information for use by processor 420.

Input component 440 may include a mechanism that permits a user to input information to device 400, such as a keyboard, a keypad, a button, a switch, etc. Output component 450 may include a mechanism that outputs information to the user, such as a display, a speaker, one or more light emitting diodes (LEDs), etc. Communication interface 460 may include any transceiver-like mechanism that enables device 400 to communicate with other devices and/or systems via wireless communications (e.g., radio frequency, infrared, and/or visual optics, etc.), wired communications (e.g., conductive wire, twisted pair cable, coaxial cable, transmission line, fiber optic cable, and/or waveguide, etc.), or a combination of wireless and wired communications. For example, communication interface 460 may include mechanisms for communicating with another device or system via a network, such as service provider network 140 and/or network 150. In one alternative implementation, communication interface 460 may be a logical component that includes input and output ports, input and output systems, and/or other input and output components that facilitate the transmission of data to other devices.

As will be described in detail below, device 400 may perform certain operations relating to publishing video content. Device 400 may perform these operations in response to processor 420 executing software instructions contained in a computer-readable medium, such as memory 430. A computer-readable medium may be defined as a non-transitory memory device. A memory device may include space within a single physical memory device or spread across multiple physical memory devices. The software instructions may be read into memory 430 from another computer-readable medium or from another device. The software instructions contained in memory 430 may cause processor 420 to perform processes described herein. Alternatively, hardwired circuitry may be used in place of or in combination with software instructions to implement processes described herein. Thus, implementations described herein are not limited to any specific combination of hardware circuitry and software.

Figure 5:
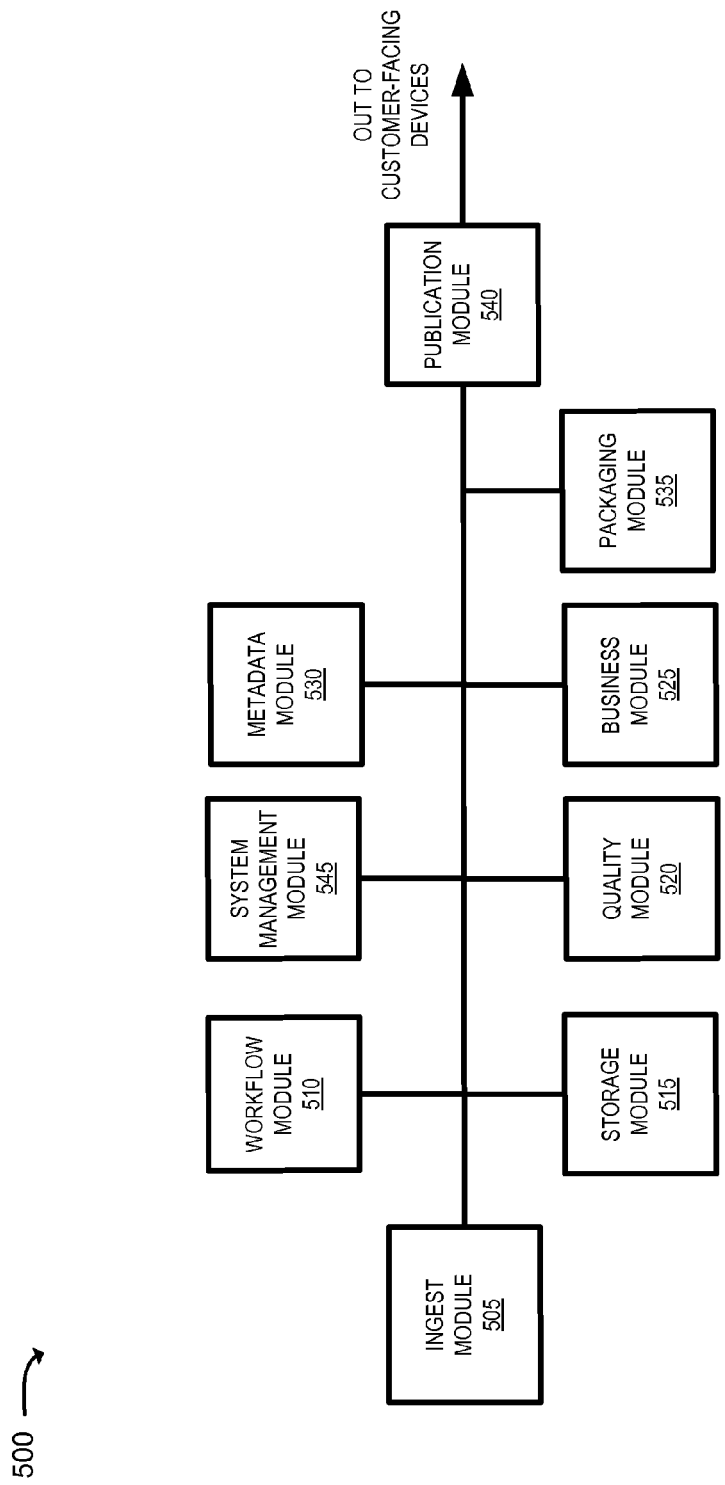
FIG. 5 is a diagram of example functional components that correspond to one or more devices of the video content management system of FIG. 2.

FIG. 5 is a diagram of example functional components 500 that correspond to one or more devices of VCM system 240. As shown in FIG. 5, components 500 may include a collection of functional components, such as an ingest module 505, workflow module 510, storage module 515, a quality module 520, a business module 525, a metadata module 530, a packaging module 535, a publication module 540, and a system management module 545. Although FIG. 5 shows example functional components of components 500, in other implementations, components 500 may contain fewer functional components, additional functional components, different functional components, or differently arranged functional components than depicted in FIG. 5. For example, one or more modules may be combined into a single module. Additionally, or alternatively, one or more functional components of components 500 may perform one or more tasks described as being performed by one or more other functional components of components 500.

In the description below, each module, of components 500, is described as being hosted by one or more devices associated with VCM system 240 for explanatory purposes. In another implementation, each of the modules may be hosted by any of the devices associated with VCM system 240 and/or one or more other devices separate from, or in combination with, the devices associated with VCM system 240.

Ingest module 505 may be hosted by ingestion server 310 and may include logic, implemented using hardware or a combination of hardware and software, that enables video content, received from content provider 130 to be ingested and/or processed. Ingest module 505 may communicate with workflow module 510 to receive instructions and/or to send notifications associated with ingesting and/or processing the video content.

Ingest module 505 may, for example, receive an instruction, from workflow module 510, to ingest the video content from content provider 130. Ingest module 505 may, in response to the instruction, cause ingestion server 310 to acquire, ingest, and/or process the video content in a manner similar to that described above in FIG. 3. Ingest module 505 may send a notification to workflow module 510 indicating that video content has been ingested and/or that the video content is available to be published.

Workflow module 510 may be hosted by VCMS controller 350 and may include workflow logic, implemented as hardware or a combination of hardware and software, that enables VCMS controller 350 to manage the manner in which video content is acquired, ingested, processed, and/or published by VCM system 240. The workflow logic may be predetermined by VCM system 240 and/or may be programmed by an operator of VCM system 240. Workflow module 510 may include one or more application programming interfaces (APIs) that enable workflow module 510 to communicate with each of the functional components of functional components 500.

In an example implementation, workflow module 510 and/or the APIs may enable components 500 to act as service oriented architecture (SOA). The SOA may permit each function and/or operation, associated with ingesting, processing, and/or publishing the video content, to be instantiated, discovered, and/or used, by workflow module 510, as a service based on a time and/or in a manner determined by the workflow logic.

Workflow module 510 may, for example, include an ingest API that enables workflow module 510 to communicate with ingest module 505 regarding ingesting and/or processing (e.g., decrypting, transcoding, etc.) video content. In another example, workflow module 510 may include a storage API that enables workflow module 510 to communicate with storage module 515 regarding storage and/or retrieval of video content while being ingested, processed, published, etc. Workflow module 510 may include a quality API that enables workflow module 510 to communicate with quality module 520 regarding performing a quality operation on video assets and/or metadata that is to be published to a destination device. Workflow module 510 may include a business API that enables workflow module 510 to communicate with business module 525 regarding generating information associated with a price structure, an availability, etc. of ingested video content. Workflow module 510 may include a metadata API that enables workflow module 510 to communicate with metadata module 530 regarding ingesting and/or processing metadata associated with the video asset. Workflow module 510 may include an encryption API that enables workflow module 510 to communicate with packaging module 535 regarding packaging a video asset (e.g., using encryption associated with DRM, CAS, etc.) for publication. Workflow module 510 may include a publication API that enables workflow module 510 to communicate with publication module 540 regarding publishing a package and/or associated metadata to a destination device associated with VPS 120. Workflow module 510 may include a system API that enables workflow module 510 to communicate with system management module 545 regarding VCM system 240 performance monitoring and/or control.

Workflow module 510 may receive a notification from one or more modules, of functional components 500, that identifies a stage, within a process, that the video asset and/or the metadata are being ingested, processed, published, etc. by one or more devices of VCM system 240. Workflow module 510 may, based on the workflow logic, send an instruction that identifies a next step, within the process, to be taken to process the video asset and/or the metadata.

For example, workflow 510 may receive a notification, from ingest module 505 and via the ingest API, that indicates that video content has been ingested by ingestion server 310. Workflow module 510 may, in response to the notification, send an instruction to quality module 520, via the quality API, that indicates that transcoded copies of the ingested video content are to be examined to ensure that the transcoded copies (e.g., of a video asset) can be played on the different types of user devices 110 (e.g., a set top box, a computer device, a wireless handheld device, a gaming device, etc.). Workflow module 510 may send, via the storage API, an instruction, to storage module 515, for the video asset to be temporarily stored in a memory (e.g., a publish memory, etc.) associated with VCM system 240.

Workflow module 510 may send, via the business API, an instruction for business module 525 to generate a price structure for the video asset based on contract information obtained, by business module 525, from content provider 130. Workflow module 510 may send, to metadata module 530, an instruction to combine the information associated with the price structure and/or other information (e.g., availability information, etc.) with the metadata. Workflow module 510 may send, via packaging module 535, an instruction for packaging module 535 to generate a package associated with the video asset using a type of encryption (e.g., DRM, CAS, etc.) identified in a video profile associated with the video asset.

Workflow module 510 may send, to publication module 535 and via the publishing API, an instruction for the package to be published to a destination device (e.g., VOD server 225, CDN server 230, etc.). Workflow module 510 may send, to publication module 535 and via the publishing API, another instruction for the metadata, associated with the asset, to be published to the destination device (e.g., VOD server 225) and/or a content catalog (e.g., hosted by catalog server 235).

Storage module 515 may include logic, implemented as hardware or a combination of hardware and software, that enables metadata and/or a video asset to be stored and/or retrieved from one or more memories, associated with VCM system 240, depending on which stage the video asset and/or metadata are being processed by VCM system 240. For example, storage module 515 may enable the video asset and/or metadata to be temporarily stored in an ingest memory and/or a metadata repository, respectively, while being ingested by ingest module 505. Storage module 515 may enable the ingested video asset to be stored, as a source video asset, in a mezzanine memory associated with VCM system 240. Storage module 515 may enable transcoded copies of the video asset to be stored in a publish memory, associated with VCM system 240 while the video asset is being checked for quality (e.g., via quality module 520) and/or encrypted for packaging (e.g., by packaging module 535) prior to publication by publication module 540.

Quality module 520 may be hosted by content processor 320 and/or publishing server 340 and may include logic, implemented using hardware or a combination of hardware and software, that enables transcoded copies of an ingested video asset to be processed, for quality control purposes, to ensure that the transcoded copies can be played on different types of user devices 110. In one example, quality module 520 may adjust screen size and/or aspect ratio to conform to screen sizes and/or aspect ratios associated with different types of user devices 110. In another example, quality module 520 may determine dimensions (e.g., length, width, position on a screen, etc.) associated with borders (sometimes referred to as a "letterbox" or "bars") within which a video asset is displayed when being played by user device 110. Quality module 520 may cause the dimensions of the letterbox and/or bars to be cropped in a manner that conforms to the screen sizes and/or aspect ratios of the different types of user devices 110. Quality module 520 may communicate with workflow module 510 to receive instructions and/or to send notifications associated with processing the copies of the ingested video content for quality control.

Business module 525 may be hosted by business server 360 and may include logic, implemented using hardware or a combination of hardware and software, that enables contract information, associated with the video asset, to be obtained from content provider 130. Business module 525 may, in a manner similar to that described above, in FIG. 3, process the contract information to generate a price structure associated with the video asset to be included in the metadata. Business module 525 may communicate with workflow module 510 to receive instructions and/or to send notifications associated with generating the price structure, identifying an availability of the video asset, and/or obtaining other information to be included in the metadata.

Metadata module 530 may be hosted by metadata processor 330 and may include logic, implemented using hardware or a combination of hardware and software, that enable copies of ingested metadata to be to be processed, for quality control purposes, to ensure that the copies are supported by different types of user devices 110. Metadata module 530 may communicate with workflow module 510 to receive instructions and/or to send notifications associated with processing the metadata and/or combining information (e.g., associated with a price structure, availability, etc.), received via business module 525, with the metadata.

Packaging module 535 may be hosted by publishing server 340 and may include logic, implemented using hardware or a combination of hardware and software, that enables video asset to be packaged and/or encrypted based on a video profile. Packaging the video asset may include copies of the video asset at different levels of resolution (e.g., standard definition, high definition, trailers, etc.), different screen parameters (e.g., screen size, aspect ratio, etc.), and/or other information (e.g., close captioning, screen border information, promotions, etc.). The copies of the video asset may, for example, include different letterbox dimensions that are cropped to conform to the different screen parameters, etc. Packaging module 535 may communicate with workflow module 510 to receive instructions and/or to send notifications associated with packaging and/or encrypting the video asset for publishing.

Publication module 540 may be hosted by publishing server 340 and may include logic, implemented using hardware and/or software, that enables a packaged video asset and/or metadata, associated with the packaged video asset, to be published. Publication module 540 may cause the packaged video asset to be sent to a destination device, such as VOD server 225 and/or CDN server 230, based on publication information associated with the destination device. Additionally, or alternatively, publication module 540 may enable metadata, associated with the packaged video asset, to be published by sending the metadata to catalog server 235 and/or VOD server 225.

System management module 545 may be hosted by VCMS controller 350 and may include logic, implemented using hardware or a combination of hardware and software, that enables a condition, associated with VCM system 240, to be detected and/or remedied. For example, system management module 545 may communicate with and/or monitor operations associated with one or more devices associated with VCM system 240. System management module 545 may send a notification, to workflow module 510, that identifies whether a condition was detected. The notification may allow workflow module 510 to modify the workflow logic in a manner that enables the video content to be ingested, processed and/or published in a manner that avoids a service disruption.

Figure 6:
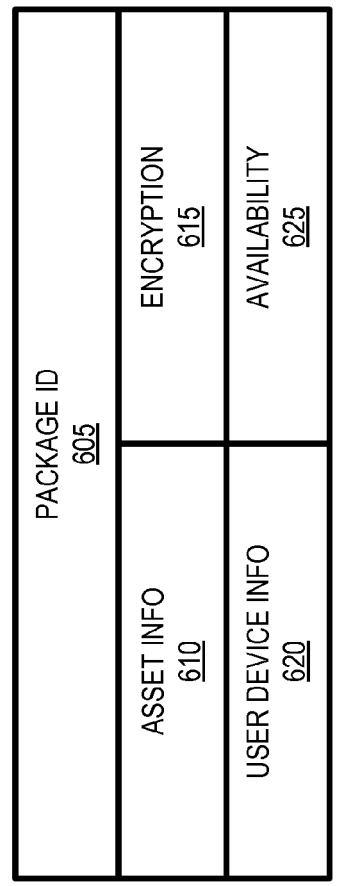
FIG. 6 is a diagram of an example video profile data structure according to an implementation described herein.

FIG. 6 is a diagram of a video profile data structure 600 that stores information associated with a video profile, according to an implementation described herein. Video profile data structure 600 may be stored in a memory associated with publishing server 340 and/or another memory associated with VCM system 240. Video profile data structure 600 includes a number of fields for explanatory purposes. In practice, video profile data structure 600 may include additional fields, fewer fields, different fields, or differently arranged fields than are described with respect to video profile data structure 600.

Video Profile data structure 600, of FIG. 6, may include a collection of fields, such as a package identifier (ID) field 605, an asset field 610, an encryption field 615, a user device information (info) field 620, and an availability field 625. Package ID field 605 may store information identifying a package to be published by publishing server 340. The information may include, for example, a sequence of characters that uniquely identifies the package. Asset info field 610 may store information associated with a video asset that is to be included in the package identified in package ID field 605. The information associated with the video asset may include information (e.g., an identifier, a file name, etc.) associated with one or more copies of the video asset. The one or more copies of the video asset may include a standard definition copy, a high definition copy, a closed captioned copy, a copy with a particular aspect ratio, a trailer associated with the video asset, etc.) that are transcoded in a format that can be supported by a particular type of user device 110 (e.g., a set top box, a computer device, a wireless handheld device, a gaming device, etc.).

Encryption field 615 may store information that identifies the manner in which the one or more copies of the video asset are to be encrypted to create a package for publication. For example, encryption field 615 may store DRM information which may be used to encrypt the one or more copies of the video asset based on a license and/or an encryption key. The license may specify when the video asset is available to be played, which type of user device 110 is permitted to play the video asset, a quantity of times the video asset can be played, etc. The DRM information may be used to encrypt the one or more copies of the video asset prior to being transmitted (e.g., via progressive download and/or an adaptive bit rate protocol, etc.) to a destination device (e.g., such as CDN server 230). In another example, encryption field 615 may store CAS information, which may be used to encrypt the one or more copies of the video asset when the video assets are being streamed to a destination device (e.g., such as VOD server 225).

User device information field 620 may store information that identifies a type of user device 110 (e.g., a set top box, a computer device, a wireless handheld device, a gaming device, etc.). Additionally, or alternatively, user device information field 620 may store information associated with a format that can be supported by the type of user device 110. Availability field 625 may store information that identifies a period of time during which the video asset can be accessible, offered, and/or distributed to user devices 110.

Figure 7:
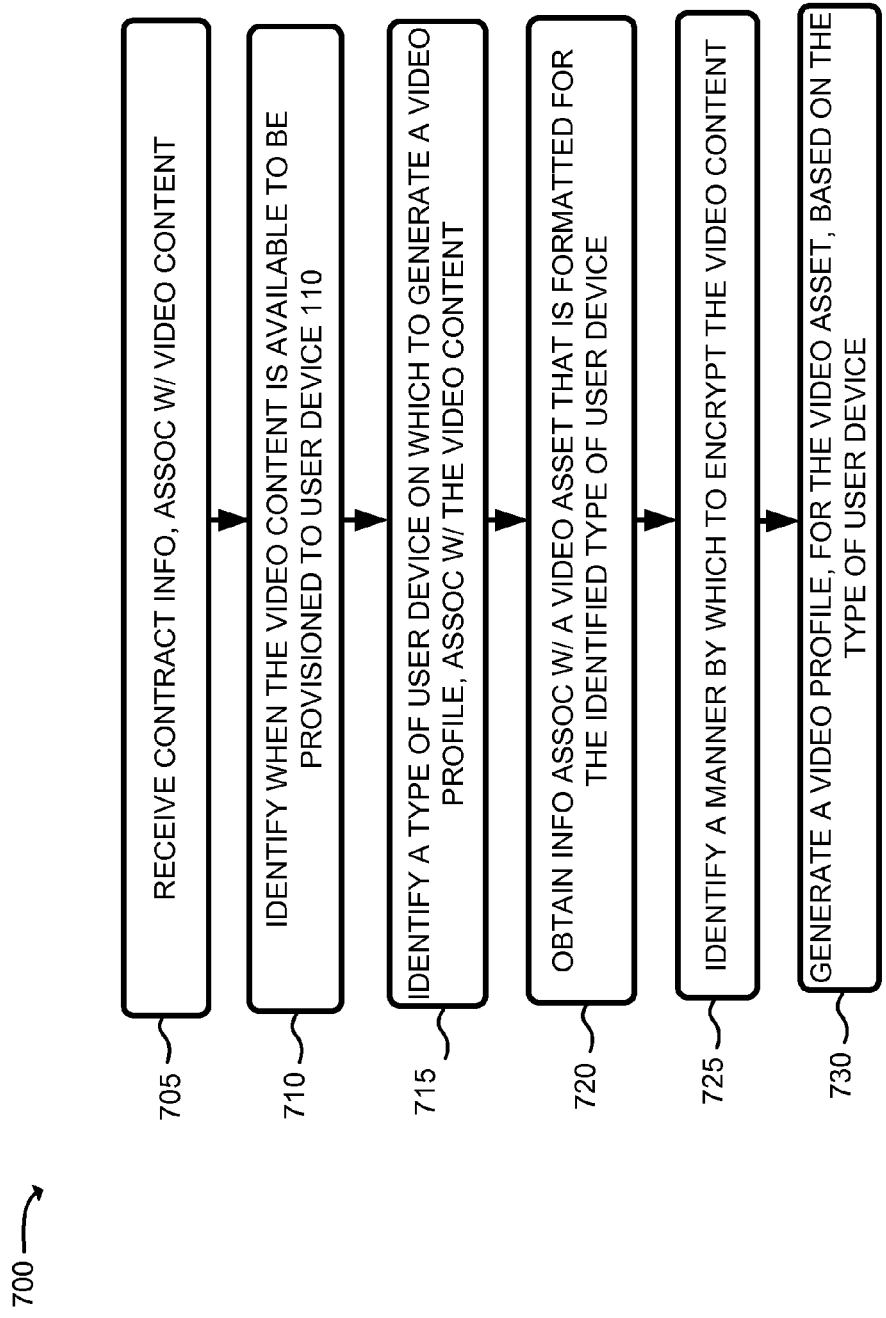
FIG. 7 is a flow chart of an example process for creating a video profile to be used to publish video content.

FIG. 7 is a flow chart of an example process 700 for creating a video profile to be used to publish video content. In one example implementation, process 700 may be performed by VCMS controller 350. In another example implementation, some or all of process 700 may be performed by a device, or collection of devices separate from, or in combination with VCMS controller 350.

As shown in FIG. 7, process 700 may include receiving contract information associated with video content (block 705) and identifying when the video content is available to be provisioned to a user device (block 710). For example, business module 525, hosted by business server 360, may communicate with content provider 130 to obtain contract information associated with video content that has been received, ingested, and/or processed by VCM system 240. The contract information may indicate when a video asset, associated with the video content, is to be made available to user devices 110. The contract information may also indicate to which types of user devices 110 the video asset is to be provisioned. Business module 525 may send the contract information, to workflow module 510 (e.g., hosted by VCMS controller 350). Workflow module 510 may receive the contract information and may identify an availability of the video asset.

As also shown in FIG. 7, process 700 may include identifying a type of user device on which to generate a video profile, associated with the video content (block 715) and obtain information associated with a video asset that is formatted for the identified type of user device 110 (block 720). For example, workflow module 510 may identify a type of user device 110 for generating a video profile. In one example, workflow module 510 may select a type of user device 110 based on the contract information. In another example, workflow module 510 may identify a type of user device 110 in a manner that does not include the contract information. Workflow module 510 may identify a format for the video asset that is supported by the type of user device 110. Workflow module 510 may obtain, from a publish memory, information associated with copies of the video asset (e.g., video asset identifiers, etc.) that have been transcoded to conform to the identified format. The copies of the video asset may include video assets associated with various levels of resolution (e.g., standard definition, high definition, etc.), screen characteristics (e.g., screen size, screen aspect ratio, screen border affects, etc.), trailers associated with the video asset, and/or other information associated with the video asset (e.g., close captioning, bundle information, advertising video, etc.).

In another example, workflow module 510 may determine that the information, associated with copies of the video asset, is not stored in the publish memory. In this example, workflow module 510 may instruct ingest module 505, hosted by ingestion server 310, to generate transcoded copies of the video asset to conform to the identified format for temporary storage in the publish memory.

As further shown in FIG. 7, process 700 may include determining a manner by which to encrypt the video asset (block 725) and generate a video profile, for the video asset, based on the identified type of user device (block 730). For example, workflow module 510 may determine that the type of user device 110 is a set top box user device 110. Based on the determination that the type of user device 110 is the set top box user device 110, workflow module 510 may determine that a package, that includes the transcoded copies of the video asset, is to be encrypted when the package is published via a video stream to a destination device, such as VOD server 225. The video stream may, for example, be encrypted using CAS-based encryption as the package is being streamed.

In another example, workflow module 510 may determine that the type of user device 110 is a different type of user device 110 than the set top box user device 110. Based on the determination that user device 110 is not a set top box, workflow module 510 may determine that the package is to be encrypted prior to being published. In this example, the package may be encrypted, using DRM-based encryption, and may be progressively downloaded and/or downloaded using adaptive bit rate streaming, to another destination device, such as CDN server 230.

Workflow module 510 may create a video profile by storing, in a data structure (e.g., profile data structure 600 of FIG. 6) information associated with the availability of the video asset, information associated with the type of user device and information associated with the manner in which the package is to be encrypted. Workflow module 510 may store, in the data structure, information associated with the transcoded copies of the video asset that correspond to a format that is supported by the identified type of user device 110. Workflow module 510 may store information associated with the package (e.g., such as a package identifier, etc.) in the data structure.

Figure 8:
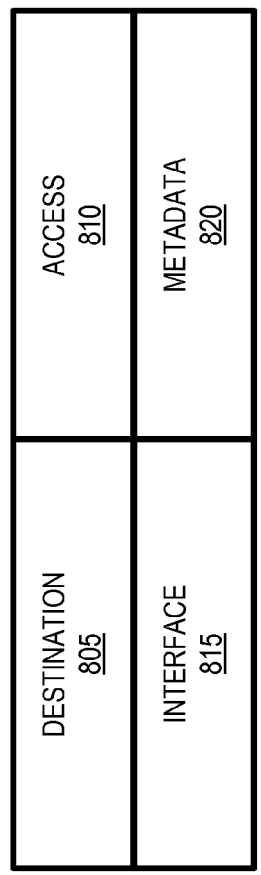
FIG. 8 is a diagram of an example publication data structure, according to an implementation described herein.

FIG. 8 is a diagram of a publication data structure 800 that stores publication information, according to an implementation described herein. Publication data structure 800 may be stored in a memory associated with publishing server 340 and/or another memory associated with VCM system 240. Publication data structure 800 may include a number of fields for explanatory purposes. In practice, publication data structure 800 may include additional fields, fewer fields, different fields, or differently arranged fields than are described with respect to publication data structure 800.

Publication data structure 800 may include a collection of fields, such as a destination field 805, an access field 810, an interface field 815, and a metadata field 820. Destination field 805 may store information associated with a destination device (e.g., VOD server 225, CDN server 230, etc.), associated with VCM system 240, to which a package is to be published. The information associated with the destination device may include, for example, an identifier associated with the destination device (e.g., a device ID, a device name, etc.), a network address (e.g., a URL, an IP address, etc.), and/or a storage location within the destination device, etc.

Access field 810 may store credentials (e.g., username, password, etc.) that may be used to access a destination device to which the package is to be published. Interface field 815 may store information that identifies an interface, associated with publishing server 340, via which the package is to be published to the destination device. Metadata field 820 may store information associated with metadata that corresponds to the video asset. For example, the information associated with the metadata may include a location within the publish memory and/or a metadata repository from which the metadata can be retrieved. The information associated with the metadata may also identify a destination device to which the metadata is to be published. The information associated with the metadata may include information associated with a format for the metadata the can be supported by the destination device and/or a user device.

Figure 9:
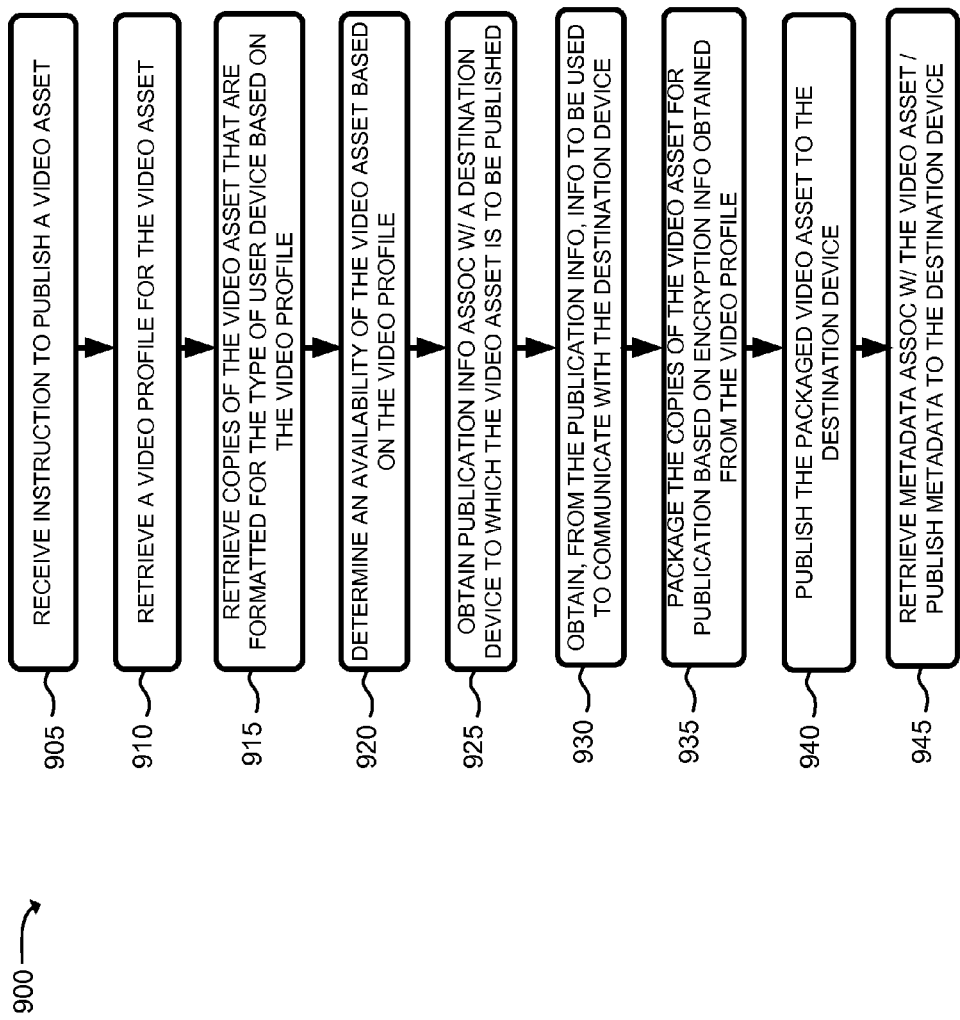
FIG. 9 is a flow chart of an example process for publishing ingested video content that allows a video provisioning system to offer and/or distribute the video content to different types of user devices.

FIG. 9 is a flow chart of an example process 900 for publishing video content that allows a VPS 120 to offer and/or distribute the video content to different types of user devices 110. In one example implementation, process 900 may be performed by one or more devices associated with VCM system 240. In another example implementation, some or all of process 900 may be performed by a system and/or device, or collection of systems and/or devices separate from, or in combination with the one or more devices associated with VCM system 240.

As shown in FIG. 9, process 900 may include receiving an instruction to publish a video asset (block 905) and retrieving a video profile associated with the video asset (block 910). For example, workflow module 510, hosted by VCMS controller 350, may receive a notification that a video asset has been ingested and/or is ready to be published to VPS 120. The notification may be received from storage module 515 when the video asset is stored in a publish memory associated with VCM system 240. Workflow module 510 may, as a result of the notification, retrieve, from a memory associated with VCMS controller 350, information associated with a video profile that corresponds to the video asset. The information associated with the video profile may be retrieved from a video profile data structure (e.g., video profile data structure 600 of FIG. 6) stored within the memory.

As also shown in FIG. 9, process 900 may include retrieving one or more copies of the video asset that are formatted for the type of user device based on the video profile (block 915). For example, workflow module 510 may identify information associated with one or more copies of the video asset that are stored in the publish memory. The one or more copies of the video asset may have been transcoded, by VCM system 240 (e.g., by content processor 320), to a format that can be supported by a type of user device 110 identified by the information associated with the video profile. The one or more copies of the video asset may correspond to different levels of resolution (e.g., standard definition, high definition, etc.), screen characteristics (e.g., screen size, screen aspect ratio, screen border affects, etc.), a trailer associated with the video asset, and/or other information associated with the video asset (e.g., close captioning, bundle information, advertising video, etc.).

In another example, workflow module 510 may determine that the one or more copies of the video asset are not stored in the publish memory. Workflow module 510 may, based on the determination that the one or more copies are not stored in the publish memory, send an instruction to content processor 320 for one or more copies of the video asset to be generated and/or transcoded to conform to the format that can be supported by the type of user device 110.

As further shown in FIG. 9, process 900 may include determining an availability of the video asset based on the video profile (block 920). For example, workflow module 510 may determine whether the video asset can be offered, accessed, and/or distributed to user devices 110 based on the information associated with the video profile. In one example, workflow module 510 may not cause the video asset to be published when the information associated with the video profile includes an indication that the video asset is not available. In another example, workflow module 510 may cause the video asset to be published when the information associated with the video profile includes an indication that the video asset is available. In yet another example, workflow module 510 may determine that the video asset is not available and may cause the video asset to be published to a destination device. In this example, the destination device may preclude the video asset from being offered, accessed, and/or distributed to user devices 110.

As yet further shown in FIG. 9, process 900 may include obtaining publication information associated with a destination device to which the video asset is to be published (block 925) and obtaining, from the publication information, information to be used to communicate with the destination device (block 930). For example, based on a determination that the video asset is available, workflow module 540 may instruct publication module to publish the video asset. Publication module 540 may receive the instruction and may retrieve, from a memory associated with publishing server 340, publication information, such as publication information stored in a publication data structure (e.g., publication data structure 800 of FIG. 8) associated with a destination device to which the video asset is to be published. For example, if the type of user device 110, with which the video profile is associated, is a set top box (e.g., based on the video profile), publication module 540 may retrieve publication information associated with VOD server 225. Publication module 540 may obtain, from the publication information, information that enables publishing server 340 to communicate with VOD server 225 in order to publish the video asset. The information that enables publishing server 340 to communicate with VOD server 225 may include a network address associated with VOD server 225 (e.g., an IP address, a URL, etc.), login credentials associated with VOD server 225 (e.g., a username, password, etc.), and/or interface information via which the one or more copies of the video asset are to be transmitted to VOD server 225.

In another example, if the type of user device 110 is different than the set top box, such as, a computer device, a wireless handheld device, etc., publication module 540 may retrieve other publication information associated with CDN server 230. Publication module 540 may obtain, from the other publication information, information that enables publishing server 340 to communicate with CDN server 230 (e.g., a network address, login credentials, interface information, etc.) in order to publish the video asset.

As still further shown in FIG. 9, process 900 may include packaging the copies of the video assets for publication based on encryption information obtained from the video profile (block 935) and publish the packaged video asset to the destination server (block 940). For example, workflow module 510, hosted by VCMS controller 350, may obtain encryption information from the information associated with the video profile and may instruct packaging module 535, hosted by publishing server 340, to encrypt the video asset based on the encryption information. Packaging module 535 may use the encryption information to encrypt the one or more copies of the video asset to create a packaged video asset. In one example, the one or more copies of the video asset may be encrypted (e.g., using CAS-based encryption), while the packaged video asset is being streamed to VOD server 230. The packaged video asset may include the encrypted copies of the video asset, terms and/or conditions that identify an availability associated with the video asset, information associated with a type of user device 110 (e.g., a set top box) on which the video asset can be played, information associated with a format (e.g., bit rate, screen size, aspect ratio, resolution level, frame refresh rate, etc.), etc. VOD server 225 may receive the packaged video asset and may store the copies of the video asset that enable the video asset to be obtained by a set top box user device 110.

In another example, packaging module 535 may encrypt the one or more video assets (e.g., using DRM-based encryption) to create the packaged video asset. Workflow module 510 may receive an indication that the packaged video asset has been created and may instruct publication module 540, hosted by publishing server 340, to transmit the packaged video asset to CDN server 230 using a progressive download protocol, an adaptive bit rate streaming protocol, or some other protocol. The packaged video asset may include the encrypted copies of the video asset, terms and/or conditions that identify an availability associated with the video asset, information associated with a different type of user device 110 (e.g., a computer device, wireless handheld device, a gaming device, etc.) on which the video asset can be played, information associated with a format (e.g., bit rate, screen size, aspect ratio, resolution level, frame refresh rate, etc.), etc. CDN server 230 may receive the packaged video asset and may store the packaged video asset that enables the video asset to be obtained by the type of user device 110 that is different than the set top box.

As also shown in FIG. 9, process 900 may include retrieving metadata associated with the video asset and publishing the metadata to the destination device or another destination device (block 945). For example, workflow module 510, hosted by VCMS controller 350, may determine whether the publication information indicates that metadata associated with the packaged video asset, is to be published to the destination device. The metadata may include images (e.g., cover art), text (e.g., descriptions, summaries, synopsis, data, etc. of the video asset), information associated with the copies of the video asset (e.g., identifiers, a title, etc.), information associated with a price structure (e.g., rental price, a sale price, a subscription price, etc.), information associated with an availability of the video asset (e.g., release dates, blackout dates, etc.), and/or other metadata. In one example, workflow module 510 may determine that the publication information includes the indication that the metadata is to be published to VOD server 225. Based on the determination that the metadata is to be published, workflow module 510 may instruct publication module 540, hosted by publishing server 340, to publish the metadata.

Publication module 540 may, in response to the instruction, retrieve, from the publish memory and/or metadata repository, one or more copies of the metadata that has been formatted in a manner that is supported by VOD server 225 and/or a set top box. Publication module 540 may transmit the metadata to VOD server 225. VOD server 225 may receive the metadata and may transmit the metadata to a store front portal (e.g., an IMG), hosted by IMG server 220, that can be accessed by the set top box. In another example, publication module 540 may transmit the metadata directly to IMG server 220. The set top box may access the store front portal to browse and/or search for the metadata. The store front portal may allow the set top box to select the metadata to obtain the video asset for playing on the set top box.

In another example, workflow module 510 may determine that the publication information includes an indication that the metadata is to be published to catalog server 235 and may instruct publication module 540 to publish the metadata to catalog server 235. Publication module 540 may, in response to the instruction, retrieve metadata, from the publish memory and/or metadata repository, one or more other copies of the metadata that have been formatted in a manner that is supported by catalog server 235 and/or a different type of user device 110 than the set top box (e.g., a computer device, a wireless handheld device, a gaming device, etc.). Publication module 540 may transmit the metadata to catalog server 235. Catalog server 235 may receive the metadata and may transmit the metadata to another store front portal (e.g., an IPG, a website, a user interface, etc.), hosted by application server 210, that can be accessed by the different type of user device 110. Additionally, or alternatively, publication module 540 may transmit the metadata directly to application server 210. The different type of user device 110 may access the store front portal to browse and/or search for the metadata. The store front portal may allow the different type of user device 110 to select the metadata to obtain the video asset for playing on the different type of user device 110.

Systems and/or methods, described herein, may enable video content, of different formats, which have been ingested and/or processed by a video content management system (VCMS), to be published to a video provisioning system. Publishing the video content to the video provisioning system may allow different types of user devices to access, obtain, and/or play the video content. The systems and/or methods may enable the VCMS to perform the publication operation by encrypting the video content video to create packaged video content. The packaged video content may include copies of the video content that are formatted to be played on the different types of user devices when the video content is available for release to user devices. The systems and/or methods may enable the VCMS to publish the packaged video content to one or more destination devices, associated with video provisioning system, from which the video asset can be obtained by the different types of user devices. The systems and/or methods may enable ingested metadata, associated with the packaged video content, to be published to a store front portal that allows the different types of user devices to access the metadata to download and/or play the video asset.

The foregoing description provides illustration and description, but is not intended to be exhaustive or to limit the implementations to the precise form disclosed. Modifications and variations are possible in light of the above teachings or may be acquired from practice of the embodiments.

While series of blocks have been described with regard to FIGS. 7 and 9, the order of the blocks may be modified in other implementations. Further, non-dependent blocks may be performed in parallel.

It will be apparent that systems and/or methods, as described above, may be implemented in many different forms of software, firmware, and hardware in the implementations illustrated in the figures. The actual software code or specialized control hardware used to implement these systems and methods is not limiting of the embodiments. Thus, the operation and behavior of the systems and methods were described without reference to the specific software code--it being understood that software and control hardware can be designed to implement the systems and methods based on the description herein.

Further, certain portions, described above, may be implemented as a component that performs one or more functions. A component, as used herein, may include hardware, such as a processor, an ASIC, or a FPGA, or a combination of hardware and software (e.g., a processor executing software).

It should be emphasized that the terms "comprises"/"comprising" when used in this specification are taken to specify the presence of stated features, integers, steps or components but does not preclude the presence or addition of one or more other features, integers, steps, components or groups thereof.

Even though particular combinations of features are recited in the claims and/or disclosed in the specification, these combinations are not intended to limit the disclosure of the embodiments. In fact, many of these features may be combined in ways not specifically recited in the claims and/or disclosed in the specification. Although each dependent claim listed below may directly depend on only one other claim, the disclosure of the embodiments includes each dependent claim in combination with every other claim in the claim set.

No element, act, or instruction used in the present application should be construed as critical or essential to the embodiments unless explicitly described as such. Also, as used herein, the article "a" is intended to include one or more items. Where only one item is intended, the term "one" or similar language is used. Further, the phrase "based on" is intended to mean "based, at least in part, on" unless explicitly stated otherwise.

What is claimed is:

1. A method comprising:
receiving, by a video content management (VCM) system, a notification that a video asset has been ingested and is ready to publish to a video provisioning system, where the video asset conforms to multiple formats that can be respectively played by a set top box and another user device, the other user device being a different type of user device than the set top box;
retrieving, from a memory associated with the VCM system and in response to the notification, a first video profile data structure corresponding to the set top box, and a second video profile data structure corresponding the other user device;
obtaining, from one or more fields contained in the first video profile data structure, first encryption information that enables the VCM system to create a first packaged asset, and obtaining, from one or more fields contained in the second video profile data structure, second encryption information that enables the VCM system to create a second packaged asset;
processing, by the VCM system, the video asset to create the first packaged asset, where the first packaged asset is playable by the set top box and can be processed by a first device, associated with the video provisioning system, that communicates with the set top box;
processing, by the VCM system, the video asset to create the second packaged asset, where the second packaged asset is playable by the other user device and can be processed by a second device, associated with the video provisioning system, that communicates with the other user device;
retrieving, from a memory associated with the VCM system, publication information from a first field in a publication data structure containing an indication that first metadata associated with the first packaged asset is to be published to the first device;
publishing, by the VCM system and based on the indication, the first metadata to the first device;
transmitting, by the VCM system and to the first device, the first packaged asset that enables the video asset to be provided, to the set top box, by the first device; and
transmitting, by the VCM system and to the second device, the second packaged asset that enables the video asset to be provided, to the other user device, by the second device.

2. The method of claim 1, where the first encryption information is associated with a cable access system (CAS) encryption standard that enables the first packaged asset to be encrypted while being streamed to the first device, and
where the second encryption information is associated with data rights management (DRM) encryption that enables the second packaged asset to be encrypted prior to being downloaded to the second device.

3. The method of claim 1, further comprising:
obtaining, from the one or more fields contained in at least one of the first video profile data structure or the second video profile data structure, information that identifies a period of time during which the video asset may be made available to one of the set top box or the other user device; and
determining that the video asset is available to be published to the at least one of the first device or the second device when a current time is within the period of time.

4. The method of claim 1, further comprising:
obtaining, from the one or more fields contained in the first video profile data structure, information associated with one or more copies of the video asset to be included in the first packaged asset, where the one or more copies of the video asset are transcoded to one or more levels of resolution or one or more bit rates; and
retrieving, from a memory associated with the VCM system, the one or more copies of the video asset.

5. The method of claim 1, where transmitting the first packaged asset further includes:
streaming the first packaged asset to the first device.

6. The method of claim 1, where transmitting the second packaged asset further includes:
downloading the second packaged asset to the second device using a progressive download protocol or an adaptive bit rate streaming protocol.

7. The method of claim 1, where one of the first packaged asset or the second packaged asset includes at least one of:
an image that corresponds to cover art associated with the video asset,
a textual description that summarizes the video asset, or
information associated with a period of time that the video asset can be played on one of the set top box or the other user device.

8. The method of claim 1, further comprising:
retrieving, from the memory, second metadata associated with the second packaged asset; and
publishing the second metadata to a network device, associated with the video provisioning system, where publishing the second metadata, to the network device, allows the other user device to access the second metadata to obtain the second packaged asset from the second device.

9. The method of claim 8, where publishing the first metadata to the first device enables the set top box to access the first metadata via an interactive media guide (IMG), and
where publishing the second metadata to the network device enables the other user device to access the second metadata, via a user interface or a webpage.

10. The method of claim 1, where the other user device includes at least one of:
a computer device,
a tablet computer,
a wireless handset device, or
a gaming device.

11. A system comprising:
one or more processors configured to:
receive an indication that a video asset has been ingested and is ready to be published to a video provisioning system,
retrieve multiple profile data structures associated with the video asset, where a first profile data structure corresponds to a set top box and a second profile data structure corresponds to another device, the other device being a different type of device than the set top box, process the video asset to create a first processed asset that can be published to a first device, associated with the video provisioning system, based on information retrieved from one or more fields in the first profile data structure, including publication information containing an indication that metadata associated with the first processed asset is to be published to the first device, process the video asset to create a second processed asset that can be published to a second device, associated with the video provisioning system, based on information retrieved from one or more fields in the second profile data structure, publish, based on the indication, the first processed asset and the associated metadata to the first device, where publishing the first processed asset enables the set top box to obtain the first processed asset from the first device, and publish the second processed asset to the second device, where publishing the second processed asset to the second device allows the other device to obtain the second processed asset from the second device.

12. The system of claim 11, where the information retrieved from one or more fields in the first profile data structure includes at least one of:

information, retrieved from a first one of the one or more fields, associated with one or more copies of the video asset that are transcoded in a format that can be played on the set top box, information, retrieved from a second one of the one or more fields, associated with a type of encryption to be used to process the video asset to create the first processed asset, or information, retrieved from a third one of the one or more fields, associated with when the video asset is to be made available to user devices associated with the video provisioning system.

13. The system of claim 11, where, when processing the video asset to create the first processed asset, the one or more processors are further configured to:

obtain, from the information retrieved from one or more fields in the first profile data structure, information associated with one or more video files, one or more images, and information associated with an availability of the video asset, retrieve the one or more video files and the one or more images, and associate the one or more video files, the one or more images, and the information associated with the availability of the video asset to create the first processed asset.

14. The system of claim 11, where the one or more processors are further configured to:

obtain, from the information, retrieved from one or more fields in the first profile data structure, encryption information to be used to publish the first processed asset, and where when publishing the first processed asset, the one or more processors are further configured to:

transmit, as a video stream, the first processed asset to the first device, where the first processed asset is encrypted, using the encryption information, as the first processed asset is being streamed to the first device.

15. The system of claim 11 where, when processing the video asset to create the second processed asset, the one or more processors are further configured to:

obtain, from the information retrieved from one or more fields in the second profile data structure, encryption information to be used to publish the second processed asset; and encrypt the video asset using the encryption information prior to transmitting the second processed asset to the second device.

16. The system of claim 11, where the one or more processors are further configured to:

obtain, information associated with the availability of another video asset from an availability field contained in a third profile data structure associated with the other video asset, determine that a current time is not within a period of time identified by the information associated with the availability of the other video asset, and store the other video asset until a future point in time, where the future point in time is within the period of time.

17. The system of claim 11, where the one or more processors are to:

retrieve publication information associated with the second device;

determine that metadata, associated with the second processed asset, is to be published to a third device based on the publication information associated with the second server device, and publish the metadata, associated with the second processed asset, to the third device, associated with the video provisioning system, where publishing the metadata, to the third device, allows the other device to select the metadata which causes the second server device to provide the second processed asset to the other device.

18. A video content management system comprising:

one or more devices configured to:

receive an indication that copies of a video asset have been ingested by the video content management system, where a first video asset, of the copies of the video asset, is transcoded to be played on a set top box, and a second video asset, of the copies of the video asset, is transcoded to be played on another user device that is a different type of user device than the set top box, encrypt the first video asset to enable the encrypted first video asset to be published to a first server device associated with a video provisioning system, encrypt the second video asset to enable the encrypted second video asset to be published to a second server device associated with the video provisioning system, retrieve publication information from one or more fields in a publication data structure associated with the first server device, where the one or more fields include:

a first field containing a network address associated with the first server device, a second field containing access credentials associated with the first server device, a third field containing information associated with an interface via which the encrypted first video asset is to be transmitted to the first server device, and a fourth field containing an indication that metadata, associated with the first video asset, is to be published to the first server device, transmit, responsive to the indication contained in the fourth field, the metadata to the first server device, transmit, using the retrieved publication information, the encrypted first video asset to the first server device, the first server device being connected to the set top box that enables the encrypted first video asset to be provided to the set top box, and transmit the encrypted second video asset to the second server device, the second server device being connected to the other user device that enables the encrypted second video asset to be provided to the other user device.

19. The video content management system of claim 18, where the one or more devices are further configured to:

retrieve other publication information, from a field in a publication data structure associated with the second server device, where the other publication information includes an indication that metadata, associated with the second video asset, is to be published to a third server device; and publish, responsive to retrieving the other publication information, the metadata to the third server device, associated with the video provisioning system, where publishing the metadata to the third server device enables the other user device to access the metadata to obtain the second video asset from the second server device.

20. The video content management system of claim 18, where the one or more devices are further to:

execute a first module, of one or more modules, that controls a logical workflow associated with an operation performed on the video asset, where the one or more modules include logic that is implemented using hardware or a combination of hardware and software, and where other modules, of the one or more modules, include at least one of:

a second module to encrypt the first video asset in a manner that enables the encrypted first video asset to be processed by the first server device or the set top box, a third module to encrypt the second video asset in a manner that enables the encrypted second video asset to be processed by the second server device or the other user device, or a fourth module to publish the encrypted first video asset or the encrypted second video asset.

21. The video content management system of claim 18, where the one or more devices are further to:

publish information, associated with data rights management (DRM) that was used to encrypt the second video asset, to a third server device associated with the video provisioning system, where publishing the information, associated with the DRM, to the third server device, enables the other user device to obtain the information associated with the DRM, from the third server device, to decrypt the encrypted second video asset.

22. The video content management system of claim 18, where the first video asset is associated with a format that corresponds to at least one of:

a first bit rate,
a first level of resolution,
a first frame refresh rate, or
a first compression/decompression (CODEC) ratio, and where the second video asset is associated with another format that corresponds to at least one of:

a second bit rate,
a second level of resolution, or
a second frame refresh rate.

\* \* \* \* \*